United States Patent [19]

Pincus et al.

[11] Patent Number: 5,270,215

[45] Date of Patent: Dec. 14, 1993

[54] COLORIMETRIC METHOD FOR DETERMINATION OF 5-HYDROXYINDOLEACETIC ACID

[76] Inventors: Matthew R. Pincus, 135 Eastern Pkwy., Brooklyn, N.Y. 11238; Harry Mukerjee, 90 Halgren Crest, Haverstraw, N.Y. 10924

[21] Appl. No.: 996,555

[22] Filed: Dec. 24, 1992

[51] Int. Cl.$^5$ .................. G01N 33/00; G01N 21/77; G01J 3/42
[52] U.S. Cl. ..................... 436/96; 436/111; 436/171; 436/813; 356/319
[58] Field of Search ............... 436/96, 111, 171, 813; 356/319

[56] References Cited

U.S. PATENT DOCUMENTS

| | | | |
|---|---|---|---|
| 3,657,118 | 4/1972 | Kraftczyk et al. | 210/658 |
| 4,863,873 | 9/1989 | Matson | 436/63 |
| 5,104,639 | 4/1992 | Matson | 424/2 |

OTHER PUBLICATIONS

Goldenberg; "Specific Photometric Determination of 5-Hydroxyindoleacetic Acid in Urine", Clin. Chem., 19, 38 (1973).

Mukerjee, et al.; "A Colorimetric Determination of 5-Hydroxyindole Acetic Acid in Urine", Clin. Chem. Acta, 209, 105 (1992).

Sawicki, et al.; "Spot Test Detection and Colorimetric Determination of Aromatic Amines and Imino Heteroaromatic Compounds with 3-Methyl-2-benzthiazolone Hydrazone", Anal. Chem., 32, 722 (1961).

Undenfriend, et al.; "The identification of 5-Hydroxy-3-indoleacetic acid in Normal Urine and a Method for its Assay", J. Biol. Chem., 216, 499-505 (1955).

Primary Examiner—James C. Housel
Assistant Examiner—N. Bhat
Attorney, Agent, or Firm—Graham & James

[57] ABSTRACT

A spectrophotometric assay for quantitative determination of 5-hydroxyindoleacetic acid in fluid samples. 3-methyl-2-benzthiazolone hydrazone is oxidized with sodium periodate to the corresponding diazonium salt. The resulting diazonium salt adds electrophilically to activated positions on indole ring of 5-hydroxyindoleacetic acid to yield azo dyes which absorb light at 510 nm.

7 Claims, No Drawings

COLORIMETRIC METHOD FOR DETERMINATION OF 5-HYDROXYINDOLEACETIC ACID

This invention relates to the determination of a marker for malignant carcinoid tumors. More particularly, this invention relates to a colorimetric method for determination of 5-hydroxyindoleacetic acid ("5-HIAA") in urine.

BACKGROUND OF THE INVENTION

5-HIAA is a tryptophan metabolite that is excreted in large quantities in the urine of individuals with malignant carcinoid tumours. Sjoederson, A., "Clinical And Laboratory Features Of Malignant Carcinoid", *Arch. Intern. Med.* 102, 136 (1958). 5-HlAA is used as a diagnostic marker for the disease. Normal values should not exceed 6 mg of 5-HIAA excreted in 24 hours. Goldenberg, H., "Specific Photometric Determination Of 5-Hydroxyindoleacetic Acid In Urine", *Clin. Chem.*, 19, 38 (1973).

Methods for determining levels of HIAA are known. The most widely used method is that of Undenfriend et al., "The Identification Of 5-Hydroxy, 3-Indoleacetic Acid In Normal Urine And A Method for Its Assay", *J. Biol. Chem.*, 216, 499–505 (1955), as modified by Goldenberg, supra. Goldenberg's modification of the method of Undenfriend et al. is based on oxidative coupling of 5-HIAA to $\alpha$-nitroso, $\beta$-napthol in a reaction catalyzed by nitrous acid to yield a purple complex which can be monitored spectrophotometrically at 540 nm. Because $\alpha$-nitroso, $\beta$-napthol also absorbs at the same wavelength as the detected species 540 nm it is necessary to remove unreacted $\alpha$-nitroso, $\beta$-napthol prior to measurement. The latter step may result in some loss of the detected species, as well as necessitating additional steps in the procedure.

Accordingly, it is desirable to develop a simplified spectrophotometric assay for 5-HIAA which avoids the necessity of separating the detected species from other reactants used in the assay prior to spectrophotometric determination. That improvement will facilitate development of automated test equipment for determining 5-HIAA.

SUMMARY OF THE INVENTION

A spectrophotometric assay for quantitative determination of 5-HIAA in fluid samples. 3-methyl-2-benzothiazolone hydrazone is oxidized with sodium periodate to the corresponding diazonium salt. The resulting diazonium salt adds electrophilically to activated positions on indole ring of 5-HIAA to yield azo dyes with absorbance at 510 nm.

DETAILED DESCRIPTION

All procedures are performed at room temperature. 5-HIAA is extracted from samples of urine with I N HCL and diethyl ether. Recovery of 5-HIAA is typically in excess of 90% of that present in samples. Phosphate buffer [pH 7.0]is added. 5-HIAA is recovered with the buffer phase. 3-methyl-2-benzahiazolone hydrazone ("MBTH") and an oxidizing agent are added to an aliquot of extraction solution together with borate buffer. In the presently preferred embodiment, the oxidizing agent is sodium periodate. It is to be expected that other periodate salts will also be effective. In addition, other oxidizing agents, such as ferric chloride or ceric sulfate can also be used. However, ferric chloride produces a lower rate of reaction, and is less useful than sodium periodate because it absorbs in the same region as the detected species. After incubation for 5 minutes, anhydrous methanol is added to clarify the reaction solution. The mixture is allowed to stand for another 5 minutes. The concentration of 5-HIAA in the sample is determined from the absorbance at 510 nm. The molar absorbtivity at this wavelength is $32.3 \times 10^4$ L mole$^{-1}$.

EXAMPLE 1

5 ml samples of urine were extracted with acidified (5 ml I N HCl in saturated NaCl) diethyl ether (25 ml). The solution was centrifuged for 2 minutes and the ether (upper) layer removed. 4 ml sodium phosphate buffer (0.1M, pH 7.0) were added to the ether phase and the mixture was shaken. The aqueous (upper) layer was removed.

0.5 ml borate buffer (1.4 g in 200 ml deionized water, titrated with 4 N NaOH to pH 8.2); 0.5 ml of MBTH solution (135 mg/dl, in deionized water) were added to 0.5 ml of the aqueous extract. The mixture was vortexed for 10 seconds and incubated for 3 minutes at room temperature. 1 ml of sodium periodate (35 mg/dl) solution was added, and the mixture again vortexed. After allowing the mixture to stand for 5 minutes, the mixture was diluted with 5 ml anhydrous methanol and allowed to stand for another 5 minutes. The absorbance of the complex was measured at 510 nm using a Beckman DV-30 spectrophotometer. All procedures were carried out at room temperature.

EXAMPLE 2

A series of five different aqueous solutions of 5-HIAA were prepared ranging in concentration from 0-100 mg/ml. Spectrophotometric determination of colored complexes revealed a linear relation between absorbance at 510 nm and concentration of 5-HIAA over a range of 0-50 mg/ml. This surpasses the range required for clinical application of the assay.

EXAMPLE 3

Ten urine specimens from ten different patients with suspected carcinoid tumors were assayed by the method of the present invention and Goldenberg's, supra, method. A correlation plot of the two sets of results revealed excellent agreement between the methods (r =0.99). Linear regression analysis by the method of least squares gave Y(invention) =0.975(Goldenberg method)+0.06.

EXAMPLE 4

The precision and reproducibility of the method of the present invention have been found to be high. The 24 hour urine sample of a patient was divided into 40 aliquots. Twenty of these aliquots were analyzed serially on the same day. (i.e., a within runs trial) The mean obtained was 2.44 mg/ml, with a standard deviation of 0.07 mg/ml and coefficient of variation of 3 percent. Another 20 samples were analyzed on each of twenty successive days to examine the between runs variability. The mean obtained was 2.39 mg/ml, with a standard deviation of 0.09 mg/ml and a coefficient of variation of 3.8%. We conclude that the method is reproducible.

EXAMPLE 5

Because the method of the present invention involves the oxidative coupling of a diazonium salt to an activated aromatic compound, 5-HIAA, the possibility of interference by other aromatic compounds was tested. Neither salicilate nor tyrosine was found to interfere with the absorbance at 510 nm of the azo dyes formed between oxidized MBTH and 5-HIAA in any of the patient samples analyzed, using the correlation method described in Example 3.

Although the present invention has been disclosed in terms of specific embodiments, those embodiments are meant to be illustrative only. The scope of the invention is set forth by the claims which are appended hereto.

We claim:

1. A colorimetric method for determining the concentration of 5-hydroxyindoleacetic acid in a fluid sample wherein
   5-hydroxyindoleacetic acid is coupled to a diazonium salt of
   3-methyl-2-benzothiazolone to form an azo dye with an absorbance band at about 510 nm.

2. The method of claim 2 wherein the diazonium salt of 3-methyl-2-benzothiazolone is obtained by oxidation with a periodate salt.

3. The method of claim 3 wherein the periodate salt is sodium periodate.

4. A method for determining 5-hydroxyindoleacetic acid in a fluid sample comprising, in order, the steps of:
   a) extracting 5-hydroxyindoleacetic acid from a fluid sample;
   b) oxidizing 3-methyl-2-benzothiazolone to form a diazonium salt of 3-methyl-2-benzothiazolone;
   c) electrophilic addition of the diazonium salt of 3-methyl-2-benzothiazolone to 5-hydroxyindoleacetic acid to form a colored azo dye; and
   d) measuring the concentration of the azo dye formed in step c) above.

5. The method for determining 5-hydroxyindoleacetic acid in a fluid sample of claim 4, wherein the step of extracting further comprises the steps of extracting with diethyl ether followed by extraction with sodium phosphate.

6. The method for determining 5-hydroxyindoleacetic acid in a fluid sample of claim 4, wherein the step of oxidizing further comprises the step of adding sodium periodate.

7. The method for determining 5-hydroxyindoleacetic acid in a fluid sample of claim 4, wherein the step of measuring further comprises the step of determining the absorbance of the sample at 510 nm.

* * * * *